US00PP32941P2

(12) United States Plant Patent
van der Meer

(10) Patent No.: US PP32,941 P2
(45) Date of Patent: Mar. 30, 2021

(54) ***ASTILBE* PLANT NAMED 'HARVANDERMEERWHITE'**

(50) Latin Name: *Astilbe chinensis*
Varietal Denomination: Harvandermeerwhite

(71) Applicant: Hans van der Meer, Nieuwe Wetering (NL)

(72) Inventor: Hans van der Meer, Nieuwe Wetering (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/873,623

(22) Filed: May 21, 2020

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./263.1, 407
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Astilbe* plant named 'Harvandermeerwhite', characterized by its tall, broadly upright and mounding plant habit; vigorous growth habit; dark green-colored leaves; freely and uniformly flowering habit; pure white-colored flowers on tall, upright and strong peduncles; and good container and garden performance.

2 Drawing Sheets

Figure 1:
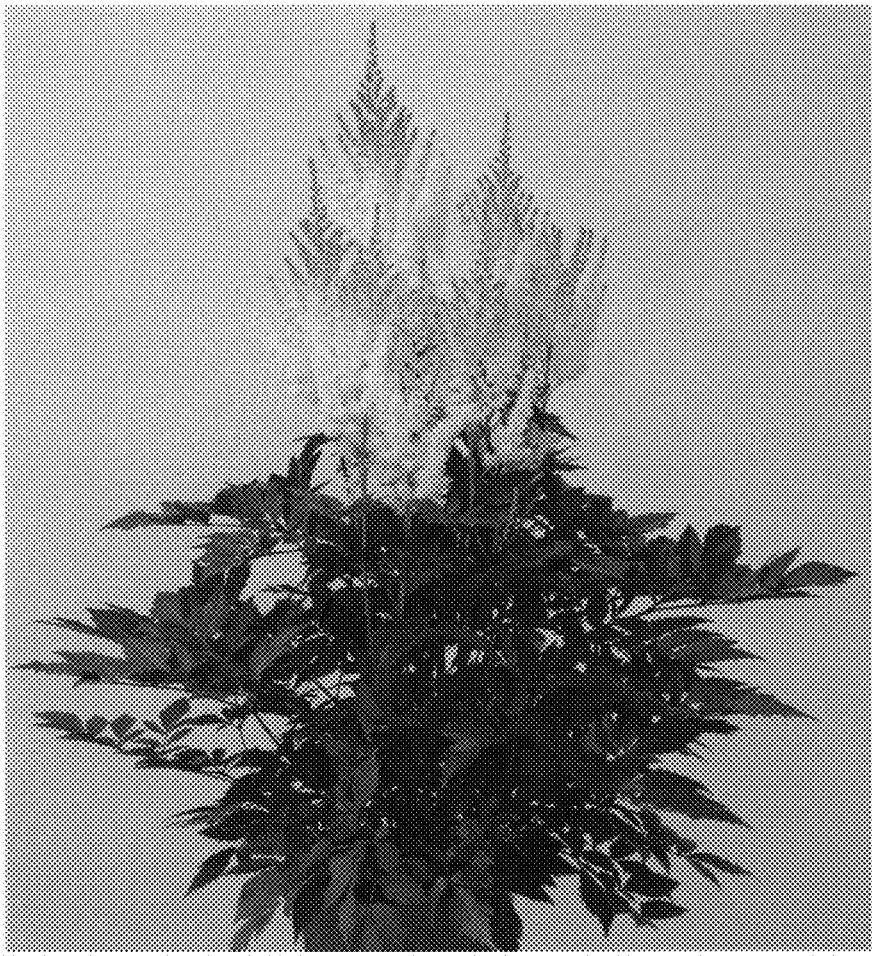

Botanical designation: *Astilbe chinensis.*
Cultivar denomination: 'HARVANDERMEERWHITE'.

CROSS-REFERENCE TO A RELATED APPLICATION AND STATEMENT REGARDING PRIOR DISCLOSURES BY INVENTOR/APPLICANT

This application claims priority to a European Community Plant Breeders' Rights application filed on Feb. 6, 2020, application number 20200384. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe chinensis* and hereinafter referred to by the name 'Harvandermeerwhite'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2013 in Nieuwe Wetering, The Netherlands, of *Astilbe*

*chinensis* 'Harvandermeer', not patented, as the female, or seed, parent with an unknown *Astilbe chinensis* seedling selection as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2015.

Asexual reproduction of the new *Astilbe* plant by vegetative divisions in a controlled nursery environment in Nieuwe Wetering, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Harvandermeerwhite'. These characteristics in combination distinguish 'Harvandermeerwhite' as a new and distinct *Astilbe* plant:

1. Tall, broadly upright and mounding plant habit.
2. Vigorous growth habit.
3. Dark green-colored leaves.
4. Freely and uniformly flowering habit.
5. Pure white-colored flowers on tall, upright and strong peduncles.
6. Good container and garden performance.

Plants of the new *Astilbe* differ primarily from plants of the female parent, 'Harvandermeer', in the following characteristics:

1. Inflorescences of plants of the new *Astilbe* are larger than inflorescences of plants of 'Harvandermeer'.
2. Flowers of plants of the new *Astilbe* are pure white in color whereas flowers of plants of 'Harvandermeer' are pink in color.

Plants of the new *Astilbe* can be compared to plants of *Astilbe chinensis* 'Vision in White', disclosed in U.S. Plant Pat. No. 18,965. In side-by-side comparisons, plants of the new *Astilbe* and 'Vision in White' differ primarily in the following characteristics:

1. Plants of the new *Astilbe* have darker green-colored leaves than plants of 'Vision in White'.
2. Inflorescences of plants of the new *Astilbe* are larger than inflorescences of plants of 'Vision in White'.
3. Flowers of plants of the new *Astilbe* are pure white in color whereas flowers of plants of 'Vision in White' are more creamy white in color.

Plants of the new *Astilbe* can also be compared to plants of *Astilbe chinensis* 'Harvandermeerrubyred', disclosed in U.S. Plant Pat. No. 31,439. In side-by-side comparisons, plants of the new *Astilbe* and 'Harvandermeerrubyred' differ primarily in flower color as flowers of plants of the new *Astilbe* are pure white in color whereas flowers of plants of 'Harvandermeerrubyred' are dark red purple in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1 of 2) is a side perspective view of a typical flowering plant of 'Harvandermeerwhite' grown in a container.

Figure 2:
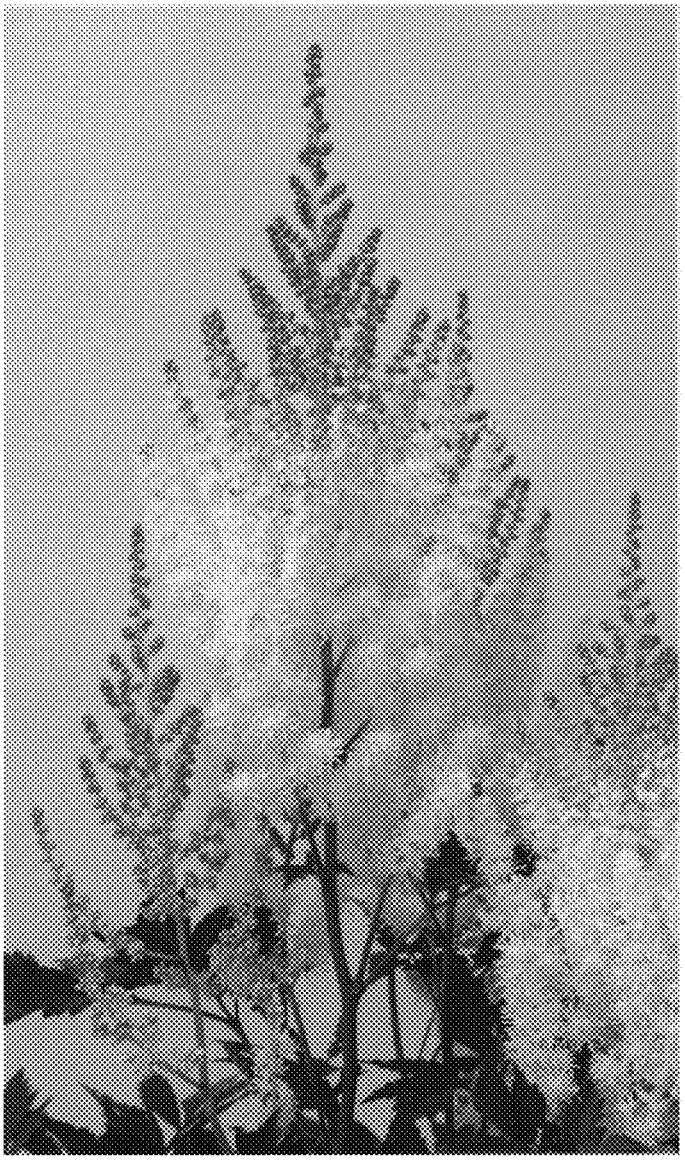

The photograph on the second sheet (FIG. 2 of 2) is a close-up view of typical inflorescences of 'Harvandermeerwhite'.

DETAILED BOTANICAL DESCRIPTION

The aforementioned photographs and following observations, measurements and values describe plants grown during the late summer in 18-cm containers in a glass-covered greenhouse in Nieuwe Wetering, The Netherlands and under cultural practices typical of commercial *Astilbe* production. During the production of the plants, day temperatures ranged from 20° C. to 40° C. and night temperatures ranged from 8° C. to 24° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe chinensis* 'Harvandermeerwhite'.

Parentage:

*Female, or seed, parent.*—*Astilbe chinensis* 'Harvandermeer', not patented.

*Male, or pollen, parent.*—Unknown *Astilbe chinensis* seedling selection, not patented.

Propagation:

*Type.*—By vegetative divisions.

*Time to initiate roots.*—About three weeks at temperatures about 20° C.

*Root description.*—Thick, fleshy; typically brown in color, actual color of the roots is dependent on substrate composition, water quality, fertilizer type and formulation.

*Rooting habit.*—Freely branching; dense.

Plant description:

*Plant form and growth habit.*—Herbaceous perennial; tall, broadly upright and mounding plant form with inflorescences held above the foliar plane; flowering stems and leaves basal; freely flowering with numerous basal branches developing per plant, dense and bushy; vigorous growth habit; and freely and uniformly flowering habit.

*Growth rate.*—Moderately rapid; from divisions, about three months are required to produce fully-grown flowering plants in containers.

*Plant height* (*soil level to top of foliar plane*).—About 48.6 cm.

*Plant height* (*soil level to top of inflorescences*).—About 74.1 cm.

*Plant width* (*spread*).—About 72.8 cm.

*Stem description.*—Length: About 33.7 cm. Diameter: About 3.5 mm. Internode length: About 16.2 cm. Strength: Strong. Aspect: Erect to about 5° from vertical. Texture and luster: Moderately pubescent; slightly glossy. Color, developing: Slightly darker than 195A. Color, developed: Close to 144A.

Leaf description:

*Arrangement.*—Alternate; biternately compound; on average, about 33 leaflets per leaf.

*Leaf length* (*excluding petiole*).—About 38 cm.

*Leaf width.*—About 29.9 cm.

*Terminal leaflet length.*—About 8.4 cm.

*Terminal leaflet width.*—About 4.3 cm.

*Lateral leaflet length.*—About 5.9 cm.

*Lateral leaflet width.*—About 2.7 cm.

*Leaf shape, in outline.*—Broadly ovate to broadly deltoid.

*Leaflet shape.*—Ovate to broadly elliptic.

*Leaflet apex.*—Apiculate to acute.

*Leaflet base.*—Short attenuate to obtuse.

*Leaflet margin.*—Biserrate; not undulate.

*Leaflet texture and luster, upper and lower surfaces.*—Moderately pubescent; slightly glossy.

*Leaflet venation pattern.*—Pinnate.

*Leaflet color.*—Developing leaflets, upper surface: Close to 137B. Developing leaflets, lower surface: Close to 147B. Fully expanded leaflets, upper surface: Close to NN137A; venation, close to 143A. Fully expanded leaflets, lower surface: Close to 147B; venation, close to 145C.

*Leaf petiole length.*—About 29.6 cm.

*Leaf petiole diameter.*—About 2.5 mm.

*Leaf and leaflet petiole strength.*—Strong.

*Leaf and leaflet petiole texture and luster, upper and lower surfaces.*—Sparsely pubescent; glossy.

*Leaf and leaflet petiole color, upper surface.*—Close to 144A; towards the base, close to 184A; at the nodes, close to 187A.

*Leaf and leaflet petiole color, lower surface.*—Close to 144A; towards the base, close to 185A; at the nodes, close to 183C.

Flower description:

*Flower type and flowering habit.*—Single rotate flowers arranged on terminal compound panicles; flowers face upright, outward or downward depending on position on the inflorescence; panicles conical in shape; freely and uniformly flowering habit with about 2,000 flowers developing per inflorescence and about 20,000 flowers developing per plant during the flowering season.

*Fragrance*.—Strong; sweet and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 3.5 mm. Diameter: About 2 mm. Shape: Ovate. Texture and luster: Smooth, glabrous; matte. Color: Sepals, close to 145C and petals, close to NN155D.

*Inflorescence height*.—About 30.1 cm.

*Inflorescence diameter*.—About 10.8 cm.

*Flower diameter*.—About 1.1 cm.

*Flower depth*.—About 6 mm.

*Petals*.—Quantity per flower: Typically five in a single whorl. Length: About 6 mm. Width: About 1 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to NN155D. Fully expanded petals, upper and lower surfaces: More white than NN155D; color does not change with development.

*Sepals*.—Quantity per flower: Typically five in a single whorl, lower 60% fused towards the base forming a campanulate-shaped calyx. Length: About 2.5 mm. Width: About 1.25 mm. Shape: Ovate. Apex: Acute. Base: Cuneate, fused. Margin: Entire. Texture and luster, upper and lower surfaces: Smooth, glabrous; matte. Color: Developing sepals, upper and lower surfaces: Close to 150D. Fully expanded sepals, upper and lower surfaces: Close to 155A; colors do not change with development.

*Peduncles*.—Length: About 29.3 cm. Diameter: About 2.5 mm. Angle: Mostly erect. Strength: Strong. Texture and luster: Moderately to densely pubescent; slightly glossy. Color: Close to 144A to 144B.

*Pedicels*.—Length: About 1 mm. Diameter: About 0.5 mm. Angle: About 45° from peduncle axis. Strength: Moderately strong. Texture and luster: Moderately pubescent; matte. Color: Close to 145C to 145D.

*Reproductive organs*.—Stamens: Quantity per flower: Typically ten; anthers basifixed. Filament length: About 3 mm. Filament color: Close to NN155A. Anther shape: Broadly ovate. Anther length: About 0.3 mm. Anther diameter: About 0.2 mm. Anther color: Close to 155C. Pollen amount: Scarce. Pollen color: Close to 155A. Pistils: Quantity per flower: Two. Pistil length: About 1.75 mm. Stigma diameter: About 0.1 mm. Stigma shape: Club-shaped. Stigma color: Close to 195D. Style length: About 1.5 mm. Style color: Close to 157A. Ovary color: Close to 145C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Harvandermeerwhite' as illustrated and described.

* * * * *